United States Patent [19]
Sukiennik et al.

[11] Patent Number: 5,894,925
[45] Date of Patent: Apr. 20, 1999

[54] MEDICAL SHARPS BLADE REMOVAL AND CONTAINMENT STRUCTURE

[75] Inventors: Corrine A. Sukiennik, Alpharetta, Ga.; Robert Case, Chicago, Ill.; H. Reiner Merz, Naperville, Ill.; James D. Morrow, Oak Park, Ill.; David G. Pasternack, Nashville, N.C.

[73] Assignee: Kimberly-Clark Worldwide, Inc., Neenah, Wis.

[21] Appl. No.: 08/590,647

[22] Filed: Jan. 24, 1996

[51] Int. Cl.⁶ .................... B65D 83/00; B65D 83/10
[52] U.S. Cl. .................. 206/356; 29/239; 30/339; 206/363; 206/359; 606/167
[58] Field of Search ................. 606/167; 30/162, 30/339; 29/239, 276; 206/354, 355, 359, 360, 356, 363

[56] References Cited

U.S. PATENT DOCUMENTS

| | | |
|---|---|---|
| D. 194,087 | 11/1962 | Jenkins . |
| D. 194,418 | 1/1963 | Gaspar . |
| D. 248,871 | 8/1978 | Forsman et al. . |
| D. 252,342 | 7/1979 | Brady . |
| D. 276,462 | 11/1984 | Villarreal . |
| 851,906 | 4/1907 | Strassburger . |
| 3,133,635 | 5/1964 | Gordon et al. . |
| 3,373,491 | 3/1968 | Montelius . |
| 3,812,743 | 5/1974 | Shaw et al. . |
| 3,825,990 | 7/1974 | Shields . |
| 4,103,572 | 8/1978 | Humble et al. . |
| 4,106,620 | 8/1978 | Brimmer et al. .......... 206/363 |
| 4,180,162 | 12/1979 | Magney ................. 206/363 |
| 4,210,145 | 7/1980 | Nestor et al. . |
| 4,244,094 | 1/1981 | Rucinski . |
| 4,318,473 | 3/1982 | Sandel ................. 206/370 |
| 4,344,531 | 8/1982 | Eldridge, Jr. et al. . |
| 4,372,182 | 2/1983 | Kolter . |
| 4,386,457 | 6/1983 | Coombs . |
| 4,395,807 | 8/1983 | Eldridge, Jr. et al. . |
| 4,466,539 | 8/1984 | Frauenhoffer . |
| 4,714,168 | 12/1987 | Johnson et al. ............ 220/1 T |
| 4,733,662 | 3/1988 | DeSatnick et al. . |
| 4,736,844 | 4/1988 | Scott et al. . |
| 4,746,016 | 5/1988 | Pollak et al. ............ 206/356 |
| 4,753,345 | 6/1988 | Goodsir et al. . |
| 4,922,614 | 5/1990 | Machida . |
| 4,985,034 | 1/1991 | Lipton . |
| 5,088,173 | 2/1992 | Kromer et al. . |
| 5,363,862 | 11/1994 | Mercier ................. 128/846 |
| 5,363,958 | 11/1994 | Horan ................. 206/356 |
| 5,449,068 | 9/1995 | Gharibian ............... 206/355 |

FOREIGN PATENT DOCUMENTS

| | | |
|---|---|---|
| 0 034 949 | 9/1981 | European Pat. Off. . |
| 0 242 035 | 10/1987 | European Pat. Off. . |
| 2 487 188 | 7/1980 | France . |
| 83/00454 | 2/1983 | WIPO . |

OTHER PUBLICATIONS

Copy of Search Report for PCT/US97/01226 dated May 29, 1997.

*Primary Examiner*—Bryon P. Gehman
*Attorney, Agent, or Firm*—Nancy M. Klembus; Dority & Manning, PA

[57] ABSTRACT

A blade removal device includes positionable hand protecting members which are movable to a position relative to a base portion for preventing injury to an operator during use of the blade removal device. A blade removal mechanism is configured in the blade removal device and is accessible through positioning of the hand protecting members. The blade removal mechanism defines a plurality of blade removal chambers disposed in communication with a blade receptacle area. Each chamber defines a blade disengaging mechanism configured to remove a blade from a surgical knife handle by inserting the blade and attached handle into the chamber and withdrawing the handle from the chamber with the blade being retained in the chamber. The blade removal device is operable for removing blades while mated with a storage section or separate from the storage section.

20 Claims, 12 Drawing Sheets ns: 5,894,925

MEDICAL SHARPS BLADE REMOVAL AND CONTAINMENT STRUCTURE

BACKGROUND OF THE INVENTION

The present invention relates to a medical sharps containment and disposal system or device, and more particularly to a hand-held surgical blade removal and containment structure.

Presently, scalpel blades are usually attached to and removed from a handle by hand. This practice creates an obvious health and safety hazard for medical personnel. Devices are apparently known and described for removing scalpel blades from their associated handles, such as described in U.S. Pat. No. 4,746,016 to Pollak et al. and U.S. Pat. No. 4,903,390 to Vidal et al. However, for one reason or the other, these devices have proven to be cumbersome or relatively difficult to operate.

Thus, what is needed in the art is a relatively simple device which allows an operator to remove and lock a used scalpel blade within the device with minimum effort and with "no touch" handling. This device should also provide for accountability of the used blades, as well as other medical sharps. The present invention provides such a device.

OBJECTS AND SUMMARY OF THE INVENTION

It is therefore a principal object of the present invention to provide a "user-friendly" scalpel blade removal device which requires minimal effort on the part of an operator.

Still a further object of the present invention is to provide a medical sharps removal device which protects the hands of the user against possible injury from the medical sharp instrument.

And still a further object of the present invention is to provide an integrated medical sharps removal and storage/accountability system.

Yet still a further object of the present invention is to provide a hand held portable medical sharps removal and containment structure which allows for relatively easy and fast change of blade sizes and types without undue delay or risk to the user.

Another object of the present invention is to provide a safe blade removal structure which provides a "no-touch" method of removing and locking scalpel blades for the user.

Yet another object of the invention is to provide a compact and versatile medial sharps containment structure that effectively accommodates all manner of medical sharps, including blades, needles, and the like.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purposes of the invention, one preferred embodiment of the present invention comprises a hand held medical sharps storage device and blade removal device for removing blades from a scalpel or knife handle wherein the scalpel handle includes a longitudinally extending boss member which engages in a longitudinal slot in the surgical blade, as commonly understood in the art.

In one embodiment of the present invention, a blade removal device is provided which may be removably mated with a storage section or used alone. The blade removal device comprises a hand holding base portion and positionable hand protecting members operably disposed relative to the base portion. In using the device, the hand protecting members can be positioned by the user to a position relative to the base portion for preventing injury to the user.

The blade removal device further defines a blade receptacle area for holding used surgical blades therein. A blade removal mechanism is configured in the blade removal device and is accessible through positioning of the hand protecting members. The blade removal mechanism defines a plurality of blade removal chambers disposed in communication with the blade receptacle area. Each chamber defines a viewable disposal location for a surgical blade within the blade receptacle area for visual accountability of the blades. Each chamber further comprises a blade disengaging mechanism configured to remove a blade from the surgical knife handle in a first and second deflection mode upon insertion of the blade and attached handle into the chamber and withdrawal of the handle from the chamber. The blade is retained and secured within the chamber. The blade removal device is operable for removing blades while mated with the storage section and also separate from the storage section.

The storage section comprises hinged halves and a locking mechanism for locking the halves in a closed position. In this embodiment, a storage area is defined between the halves. It may also be desired that at least one of the halves comprise a sharps accountability device such as a foam or a magnetic pad having labeled positions defined thereon for counting and retaining medical sharps, e.g. needles. The storage section may preferably comprise a receiving well defined therein for mating engagement with the blade removal device. The hand holding base portion of the blade removal device is slidably engaged within the receiving well. In this embodiment, the hand protecting members comprise hinged locking cover components which open to a position substantially transverse to a longitudinal plane through the hand holding base portion. In this manner, the blade removal mechanism is accessible by opening the cover components.

The blade removal device, or at least particular components thereof, may be formed of a substantially transparent material so that an operator can view the fullness state of the blade removal device without opening the cover components.

Each blade removal chamber of the blade removal mechanism is uniquely configured for quick and safe disengagement of the blade from its respective knife handle and for positively retaining the blade within the chamber. Each chamber comprises a rigid guide post centered between oppositely facing rigid blade contacting members. The blade contacting members include slanted surfaces which cooperate with the guide post to define an initial slanted path into the chamber for the surgical blade. The guide post contacts the boss member of the knife handle with at least one of the slanted surfaces contacting the blade on either side of the boss member upon the blade and handle being inserted into the initially slanted path. This action causes the blade to bow or deflect away from the knife handle in a first deflection mode of the device. The chamber further defines an essentially straight path merging from the slanted path whereby upon further insertion of the blade into the chamber, the blade is forced along the straight path with the slanted surfaces thereby forcing the blade away from the boss member until the blade disengages from the boss member in a second deflection mode of the device. The guide post further defines a recess to allow the blade to fall away from the boss member upon disengaging therefrom. The guide post further includes a retaining lip defined thereon to hold the surgical blade within the chamber upon removal of the handle from the chamber and upon any subsequent orientation or positioning of the device.

Each chamber of the blade removal mechanism may comprise rigid guide walls disposed along the chamber to maintain the blade and handle centered on the guide post and to limit movement of the knife handle within the chamber. Desirably, each chamber is defined by oppositely facing rigid plane members. Each plane member, with the exception of the extreme end plane members, comprises a guide post formed on one face thereof and the blade contacting members formed on the opposite face thereof.

The hand holding base portion of the blade removal device may also comprise a blade abutment member disposed along the bottom of the blade receptacle area.

As mentioned, the blade removal device may be mated with a storage section which comprises hinged halves and a locking mechanism for locking the halves in a closed position. In this embodiment, the storage area is defined between the halves. It may also be desired that at least one of the halves comprise a sharps accountability device such as a foam or a magnetic pad having labeled positions defined thereon for retaining medical sharps. The storage section may also have a length and a width so as to fit within an operator's shirt or jacket pocket. The storage section may comprise a receiving well defined therein for mating engagement with the blade removal device. The hand holding base portion of the blade removal device is slidably engaged within the receiving well. In this regard, the storage section also acts as a "handle" for the blade removal device. In this embodiment, the hand protecting members comprise hinged locking cover components which open to a position substantially transverse to a longitudinal plane through the hand holding base portion and handle section. In this manner, the blade removal mechanism is accessible by opening the cover components while the user grasps the storage section. Thus, the user's hand is always protected in the area behind or rearward of the hand protecting members. Even if the user removes the handle section from the blade removal device and uses the blade removal device alone, the area behind the hand protecting members defines a "safe" area for the user's hand.

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
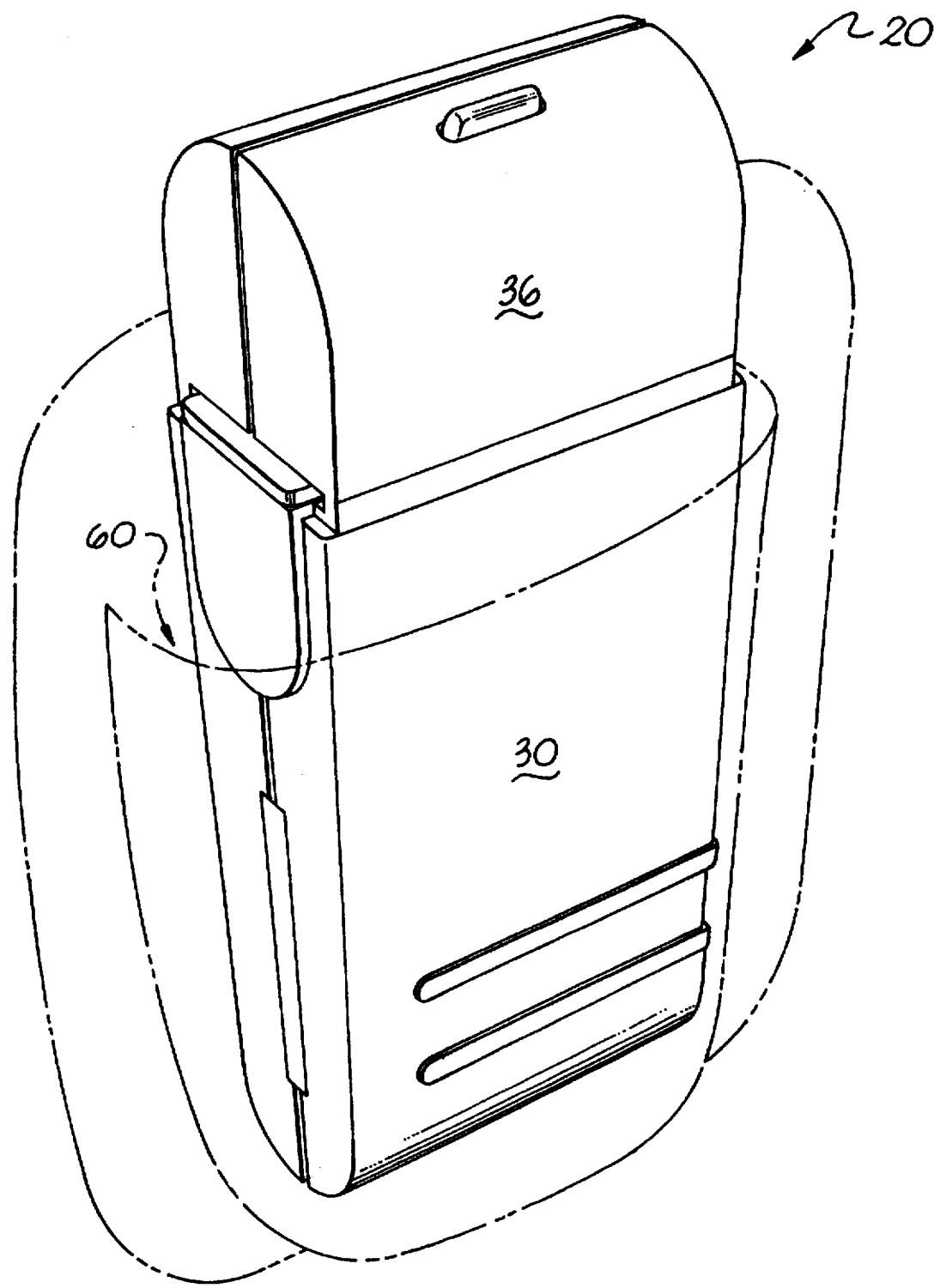
FIG. 1 is a perspective view of an embodiment of the invention represented schematically as stored in an operator's pocket.

Reference will now be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. The numbering of components in the drawings is consistent throughout the application, with the same components having the same number in each of the drawings.

Those skilled in the art are familiar with and understand the configuration and operation of conventional scalpel blades and associated knife handles. Accordingly, a detailed explanation of the scalpel blade and handle is not necessary for purposes of this disclosure. However, a brief description of the operation of conventional scalpel blades and knife handles may be useful as background for the present invention.

Figure 10A:
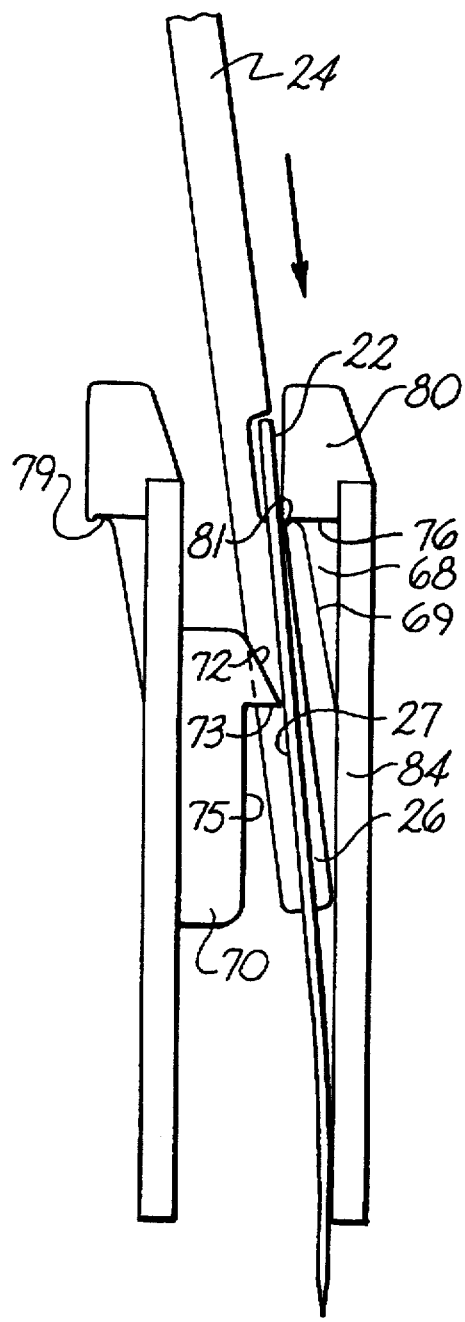
FIGS. 10a through 10c are sequential operational views illustrating use of the invention to disengage a blade from a surgical blade handle and to lock and store the blade within the removal device.
Figure 10B:
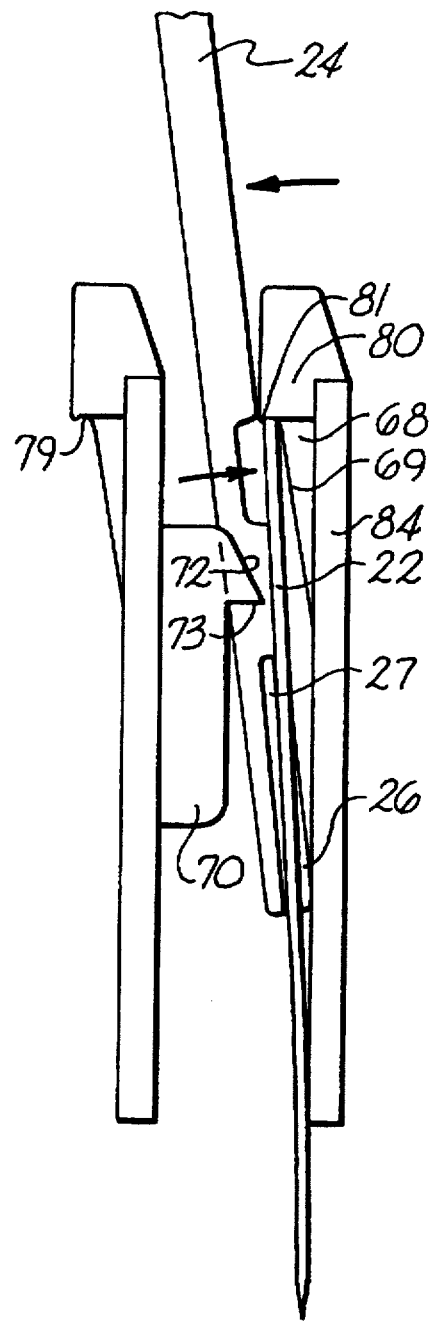
Figure 10C:
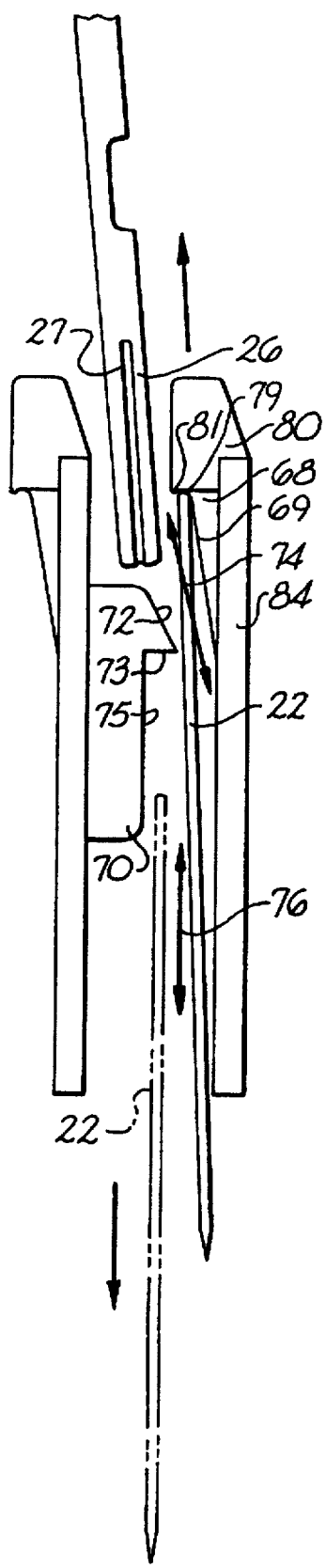

A brief description of the operation and configuration of a conventional scalpel blade and handle will facilitate an understanding of the present invention. Referring particularly to FIGS. 5 and 10a through 10c, conventional scalpels have scalpel blades 22 which engage on a longitudinally extending boss member 26 defined on a knife handle 24. As can be seen generally in the FIG. 5, blades 22 include a relatively flat rear portion having a longitudinal slot or aperture 28 defined therein. Slot 28 has a wider rear portion for initially engaging the boss member 26 of handle 24 and a relatively narrow forward portion. The narrow forward portion of slot 28 engages in an undercut portion 27 defined in boss member 26 (FIGS. 10a through 10c). When the blade and handle are completely engaged, the boss member 26 is inserted within blade aperture 28 with the rear edge of the blade aperture snapped over the rear of the boss member 26.

In order to remove blade 22 from handle 24, the rearward section of blade 22 in the area of the wider portion of aperture 28 must be separated from the handle to disengage the rear end of blade 22 from the boss member 26. Subsequently, the blade 22 can be moved relatively forward until the undercut section 27 of boss member 26 clears the narrow forward portion of blade aperture 28. Blade 22 is then free to be cleared from handle 24.

The present invention is intended for use with the conventional scalpel blade and handle arrangement described above, but the invention is in no means limited to use with such conventional items. The present invention may be appropriate for use with any manner of medical sharp devices, and any and all such uses are contemplated within the scope of the invention.

An embodiment of the present invention is illustrated generally in FIG. 1. The present inventive blade removal device 36 is shown mated with a storage section 30 to form a two-part storage and removal device 20. Device 20 may be sized so as to fit easily within a shirt or jacket pocket 60 of the user of the device.

Figure 2:
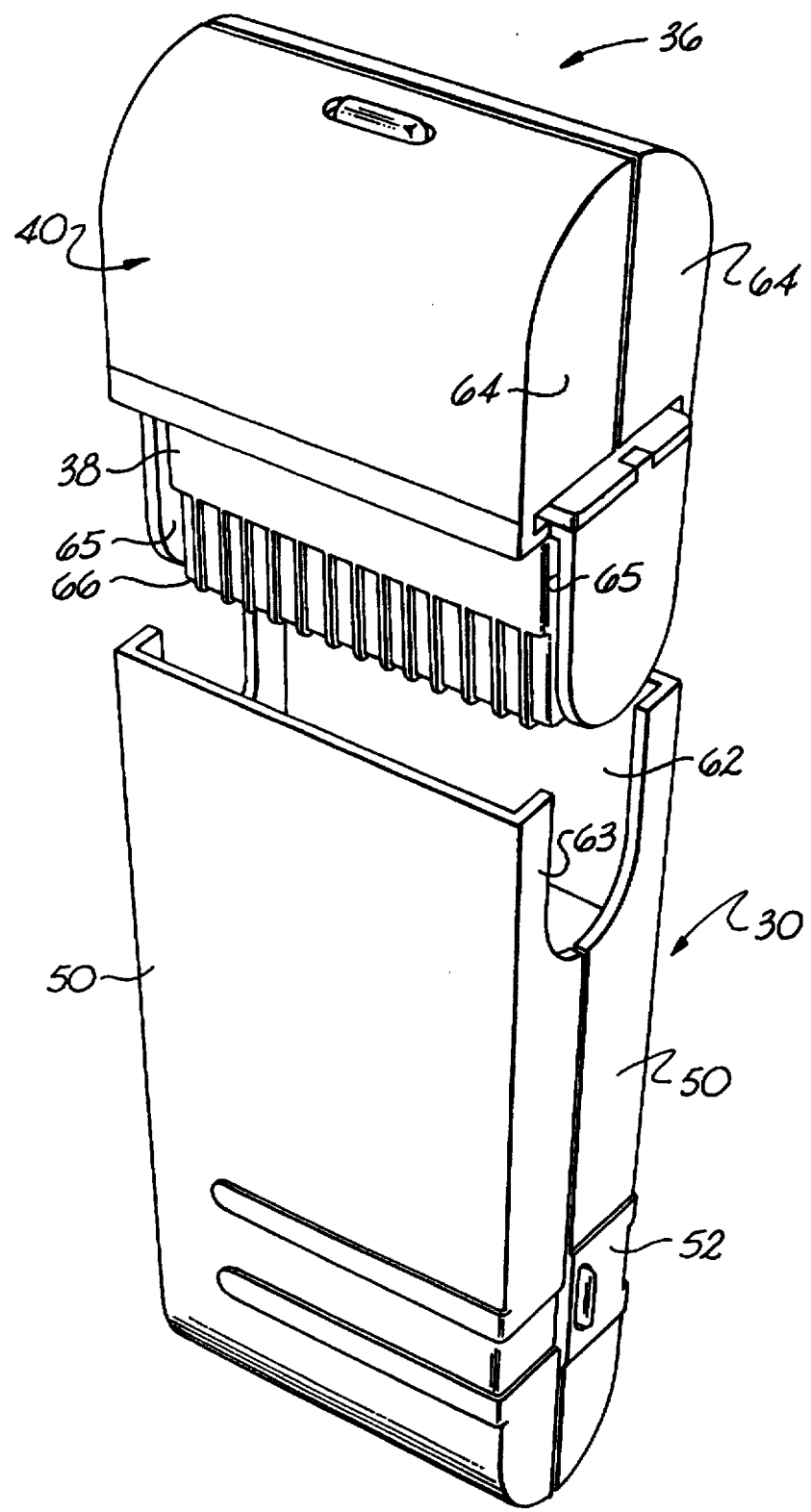
FIG. 2 is a component view of the device shown in FIG. 1 particularly illustrating the storage section and blade removal device removed from the storage section.

Referring particularly to FIG. 2, it can be seen that blade removal device 36 is removably mated to storage section 30. In this regard, storage section 30 includes a receiving well 62 defined therein. Well 62 is defined by side members 63 which engage in slotted portions or grooves 65 defined in a base member of blade removal device 36. It should be understood that any manner of locking engagement between blade removal device 36 and storage section 30 is contemplated within the scope of the invention and that the embodiment illustrated with engaging side member 63 and receiving slots 65 is but a mere preferred embodiment of the invention.

Figure 3:
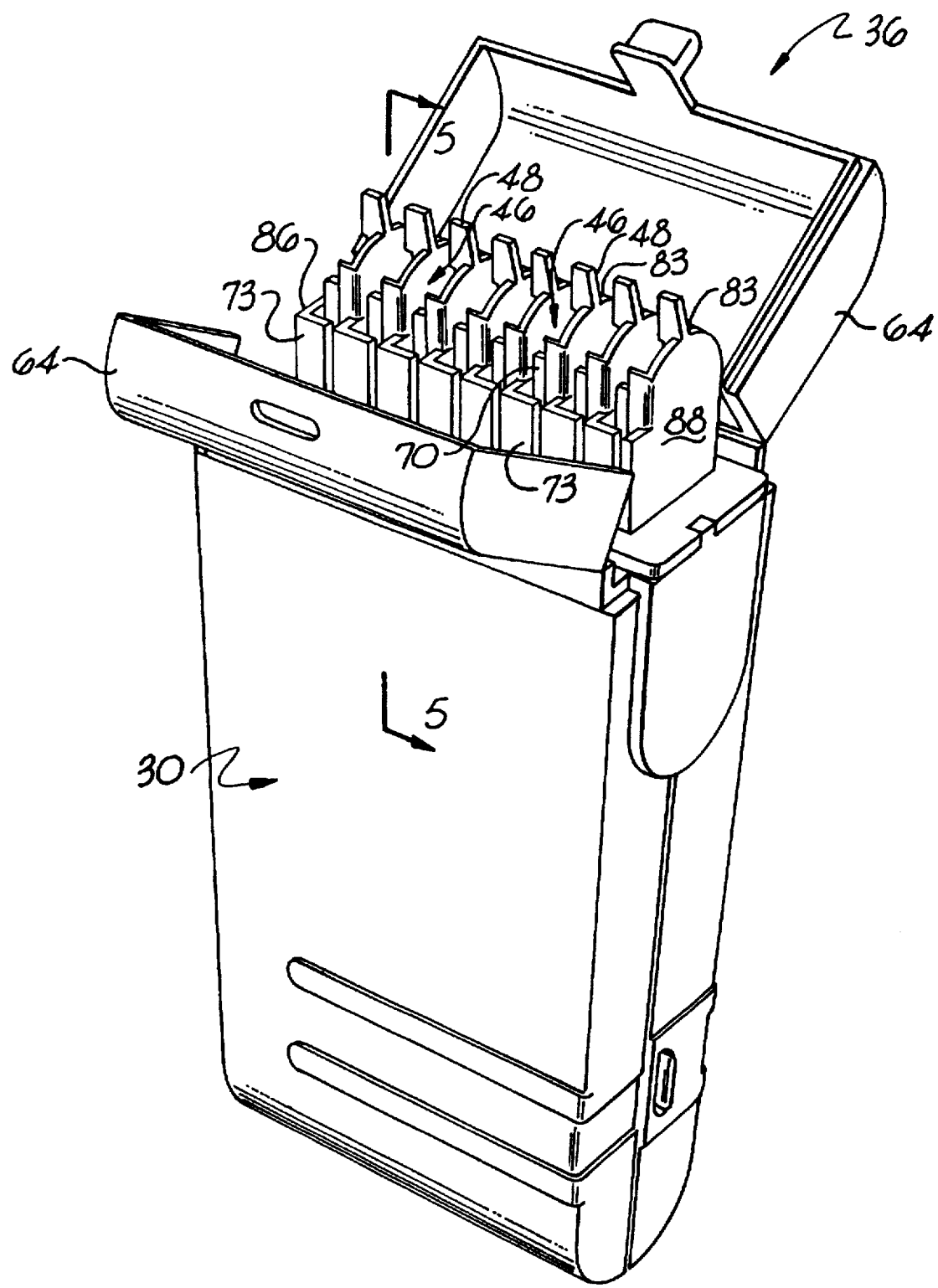
FIG. 3 is a perspective view of the blade disposal device mated with the storage section particularly illustrating the operable position of the hand protecting members.
Figure 4:
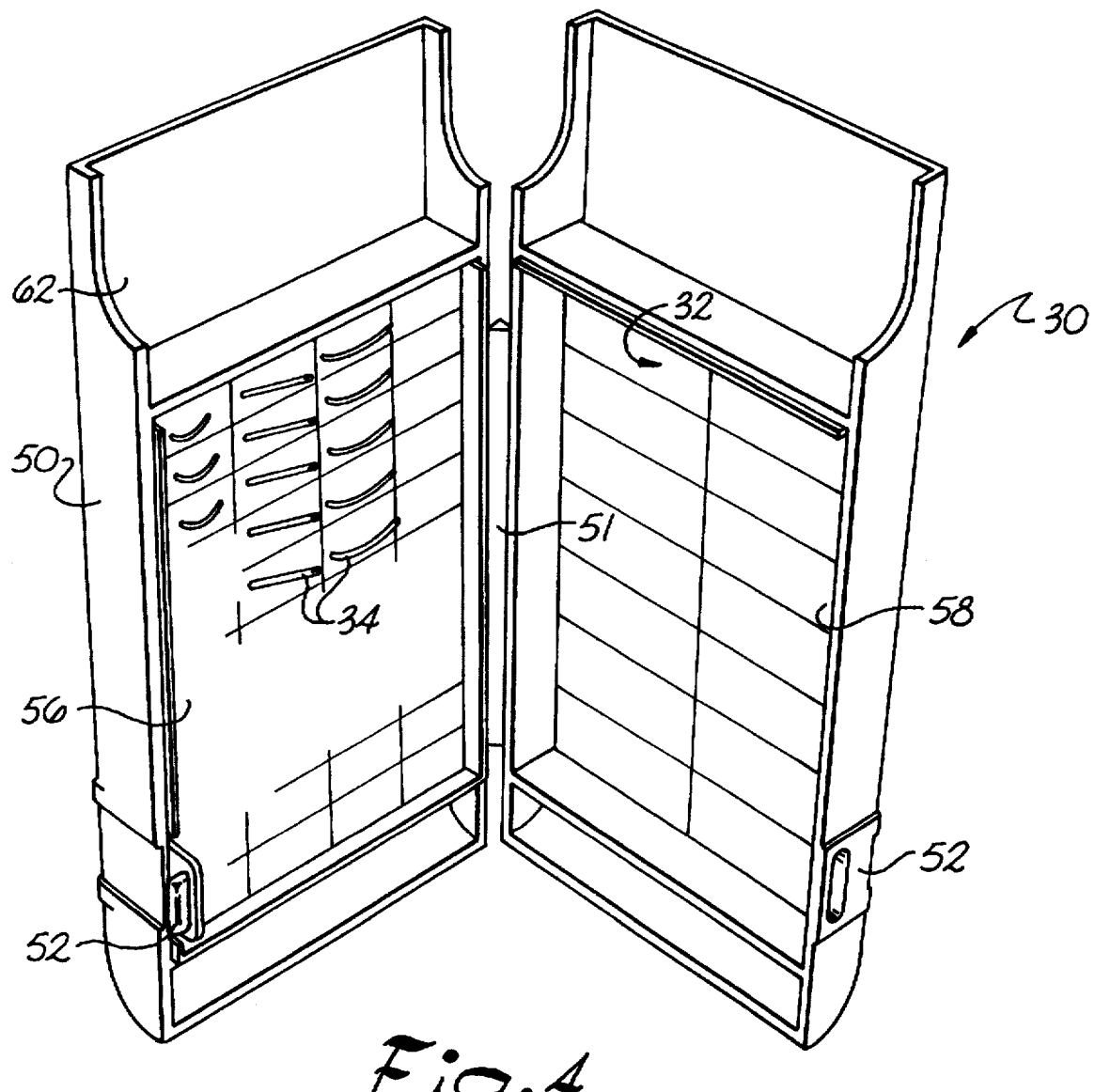
FIG. 4 is a more detailed view of the storage section particularly illustrating the medical sharps storage area defined between the halves of the storage section.

Referring particularly to FIGS. 2 through 4, storage section 30 preferably comprises hinged halve members 50 and a locking mechanism 52 for locking halves 50 in a closed position as illustrated in FIGS. 2 and 3. Locking mechanism 52 includes a male portion 52a which positively seats in female receiving portion 52b. This "through-hole" design for locking mechanism 52 ensures that storage section 30 remains closed should the device be dropped. Hinged halves 50 may be hinged by a living hinge 51 as illustrated in FIG. 4, or any suitable hinging device. Engaging shoulders or edges 53 may be provided on opposing surfaces of the halves 50 to ensure precise alignment and engagement of halves 50. Additionally, locking mechanism 52 can comprise any conventional locking device for securing halves 50 in a closed position.

Once storage section 30 is removed or separated from blade removal device 36, halves 50 can be opened to provide access to a storage area or space 32 for medical sharps defined between halves 50, as particularly illustrated in FIG. 4. Storage area 32 also preferably includes at least one sharps accountability device, such as a foam pad 56 or a magnetic pad 58. The pads are preferably divided or lined to define precise storage locations for medical sharps such as needles 34 illustrated in FIG. 4. Any combination of magnetic or foam pads 58, 56 can be utilized within storage area 32. Also, the pads may be lined or otherwise segmented in any useful accountability or counting scheme. Additionally, the device is not limited to use for storage and accountability of any particular type of medical sharps 34. For instance, needles, blades, staples, and the like can be stored within storage section 30.

Figure 9:
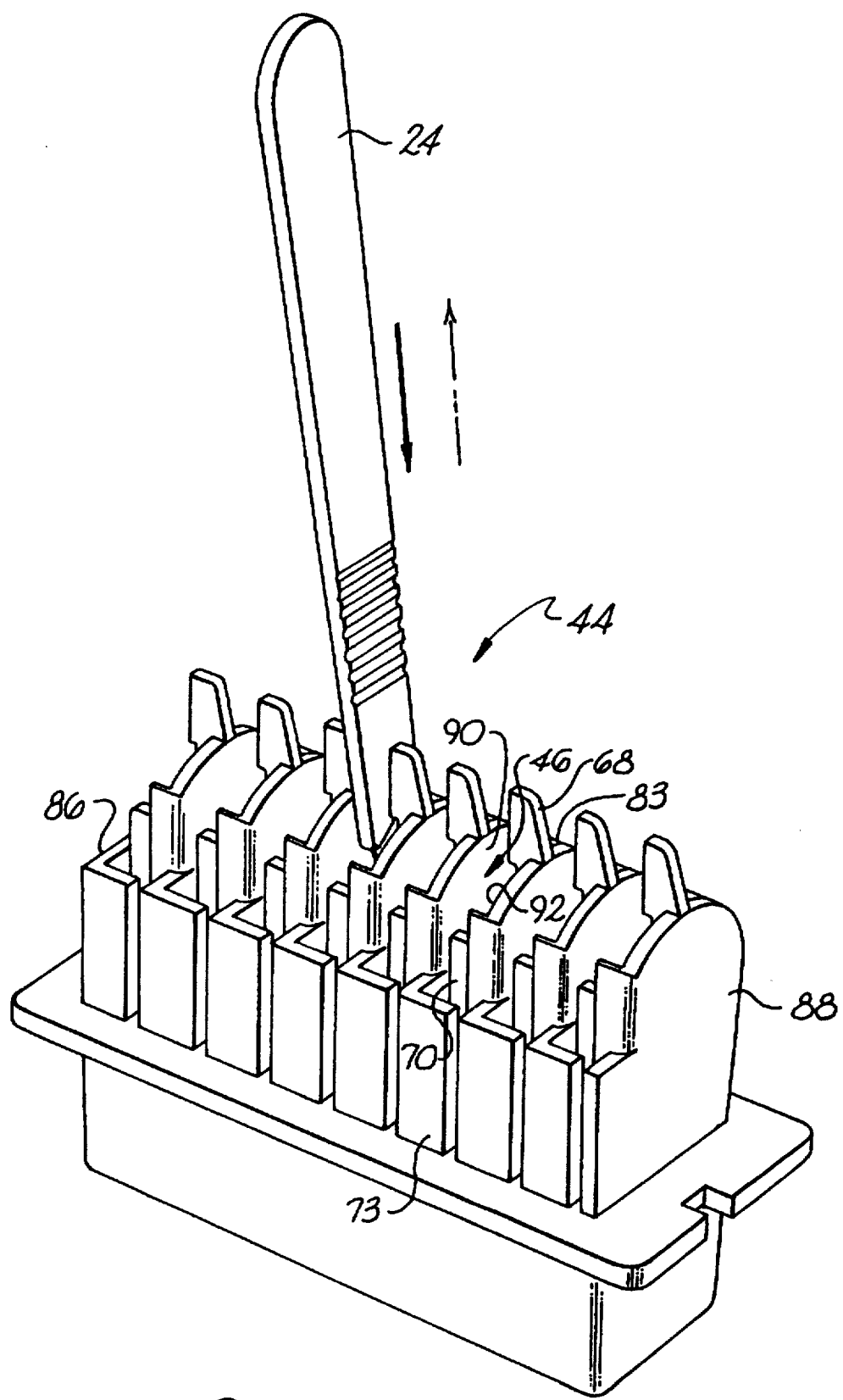
FIG. 9 is a perspective view of the blade removal device according to the invention particularly illustrating operation of the knife handle within the device to disengage the blade therefrom.

The blade removal device 36 according to the invention is particularly illustrated in FIGS. 2, 3, and 9. Device 36 includes a hand holding base portion 38 and hand protecting members 40 operably attached thereto. Hand protecting members 40 preferably comprise hinged cover components or members 64. Cover members 64 are hinged to base portion 38 through, for example, a living hinge mechanism. Hand protecting members 64 are closable to a position indicated in FIG. 2 and maintained closed by an appropriate locking mechanism, such as the positive engaging throughhole device 35. Any appropriate locking mechanism may be utilized in this regard. Alignment shoulders or edges 37 are also included to ensure precise alignment and engagement of the members 64.

Figure 3A:
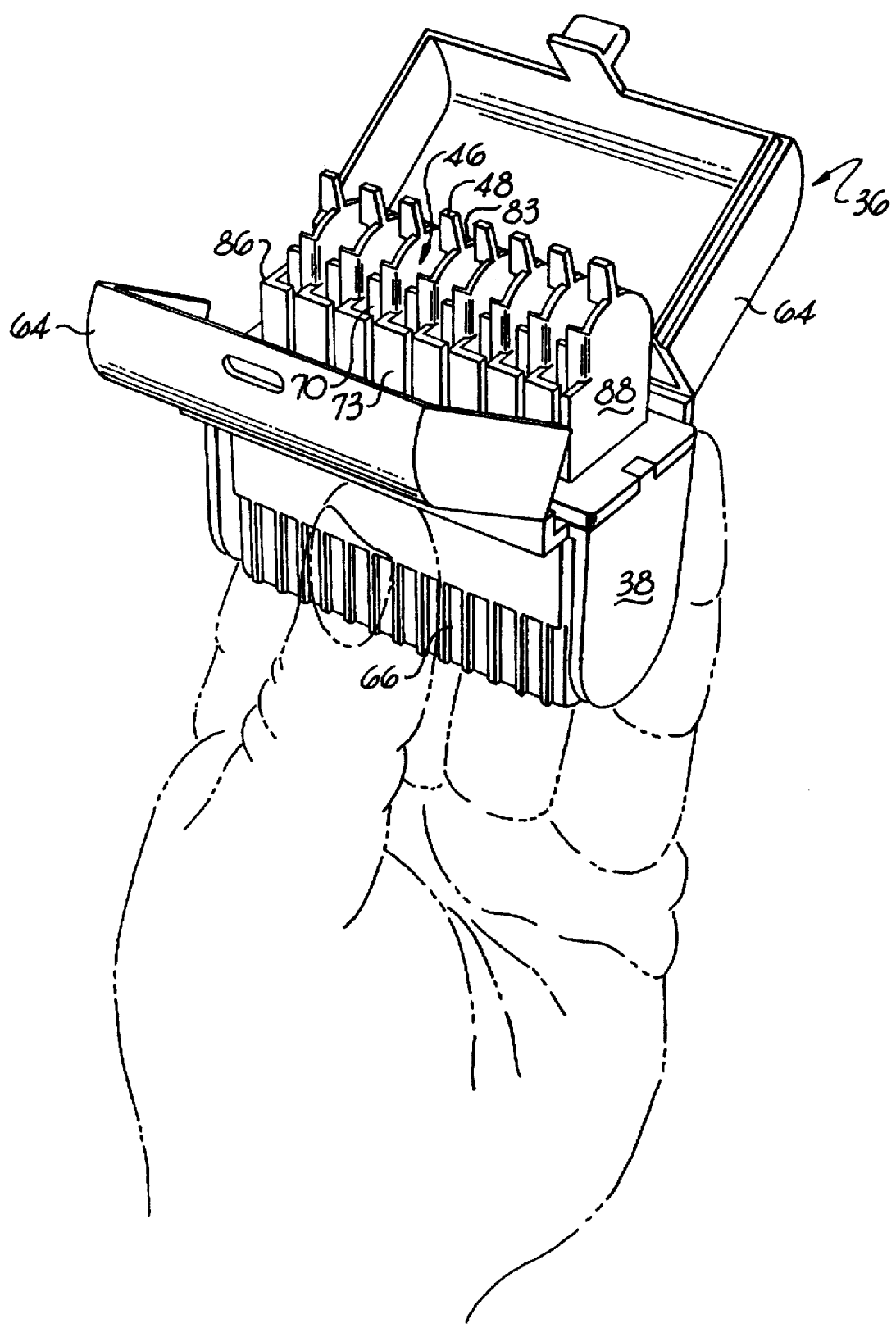
FIG. 3a is a perspective view of the blade removal device being held in the hand of an operator.

Cover members 64 are operably movable to a position substantially transverse to a plane through base portion 38, as illustrated in FIGS. 3 and 3a. Cover members 64 define a protected zone for the hand of a user using the device, as illustrated particularly in FIG. 3a.

Blade removal device 36 may be used separately from storage section 30, as particularly illustrated in FIG. 3a. In use in this manner, the user grasps device 36 about hand holding base portion 38. Again, cover members 64 fold back or are positionable so as to define a protected zone for the operator's hand. Blade removal device 36 may also be mated with storage section 30, as shown in FIG. 3. Thus, it should be understood that storage section 30 not only provides a convenient and readily accessible storage device for medical sharps, but also serves as an extension handle for blade removal device 36.

Figure 5:
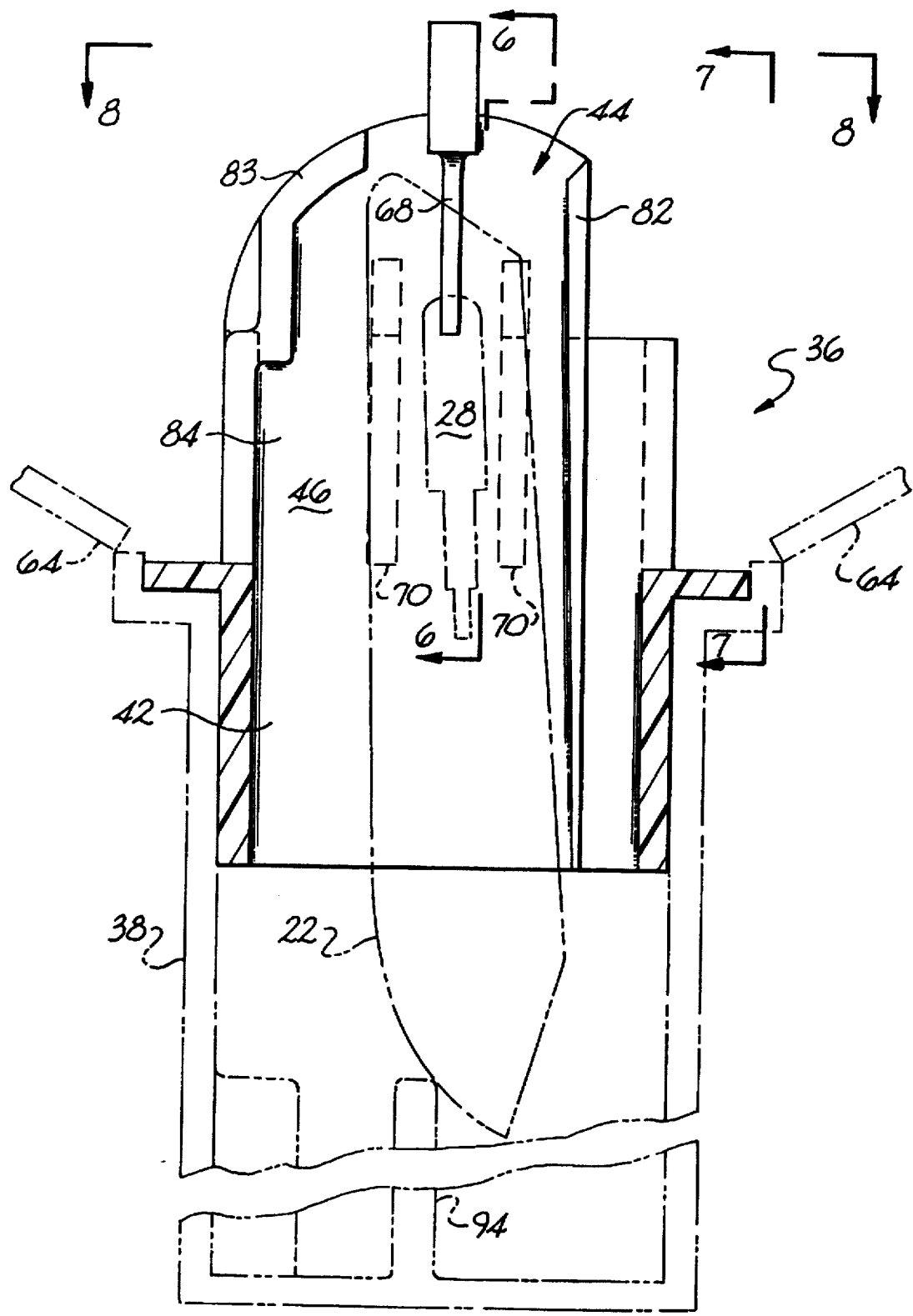
FIG. 5 is a cross-cut view of one of the blade removal chambers defined in the blade removal device and illustrates the position of the blade within the chamber.
Figure 6:
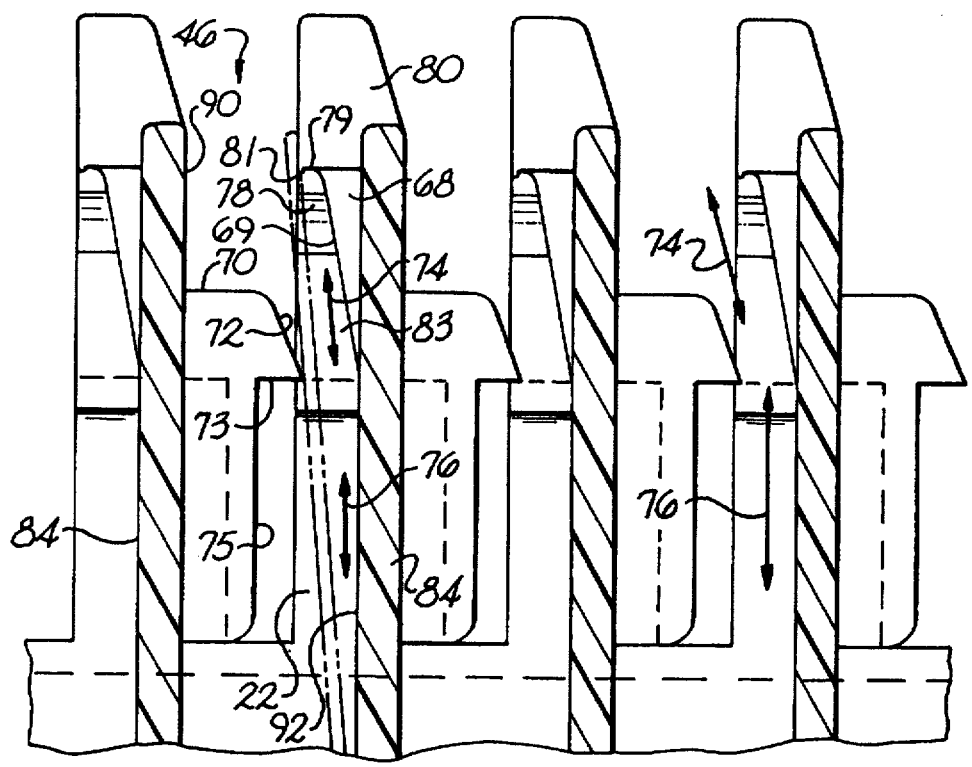
FIG. 6 is a view of the device illustrated in FIG. 5 taken along the lines indicated.
Figure 7:
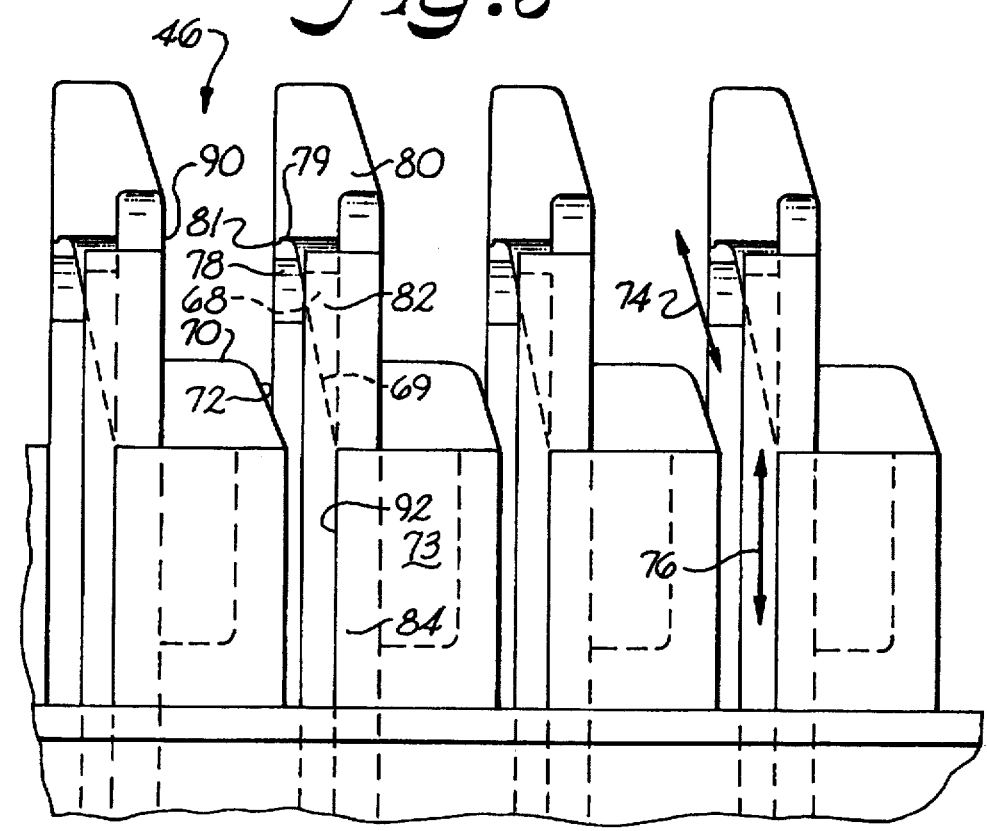
FIG. 7 is a perspective view of the device illustrated in FIG. 5 taken along the lines indicated.

Blade removal device 36 further defines a blade receptacle area 42 defined therein, as particularly illustrated in FIG. 5. As will be explained in more detail below, the blade receptacle area 42 is preferably defined in hand holding base portion 38 and is in communication with the plurality of blade removal chambers or slots 46, as discussed more fully below. In this regard, blade removal device 36 may be formed of a relatively transparent material, including hinged cover members 64, so that a user can remotely view the accountability or fullness state of the device without opening cover members 64 or otherwise manipulating the device. This feature will be explained in more detail below.

Blade removal device 36 further includes a blade removal mechanism, generally 44 (FIG. 5), configured therein providing a means for removal of a surgical blade 22 from a knife handle. It should be understood that any manner of blade removal mechanism may be incorporated in device 36. Blade removal mechanism 44 is accessible through positioning of the hand protecting members 64, as particularly illustrated in FIG. 3.

Blade removal mechanism 44 is particularly illustrated in FIGS. 5 through 10. In this embodiment, blade removal mechanism 44 defines a plurality of blade removal chambers 46 disposed in communication with blade receptacle area 42, as particularly illustrated in FIG. 5. Each chamber 46 defines a viewable disposal location for a surgical blade 22 within blade receptacle area 42 for visual accountability of the blades. For example, the embodiment of the device illustrated in FIG. 9 includes eight individual blade removal chambers 46 which define eight distinct storage locations for used surgical blades. As particularly illustrated in FIG. 5, a portion of the stored blade is contained within chamber 46 while a portion of the blade extends into the blade receptacle area 42. In this manner, the user can readily ascertain which of the chambers 46 is free to receive a used blade.

Each blade removal chamber 46 comprises a blade disengaging mechanism to remove blades 22 from surgical knife handles 24 in a first and second deflection mode by insertion of the blade 22 and attached handle 24 into chambers 46 and subsequent withdrawal of the handle 24 from the chamber 46 with blade 22 being retained in the chamber 46, as explained more fully below.

Referring particularly to FIGS. 5 through 8 and FIGS. 10a through 10c, the blade removal mechanism 44 defined in each chamber 46 comprises a rigid guide post 68 which is centered between oppositely facing rigid blade contacting members 70. Guide post 68 and blade contacting members 70 are laterally offset from each other so as to define an initially slanted path 74 for surgical blade 22, as particularly illustrated in FIGS. 6, 7, and 10a through 10c. Guide post 68 includes a longitudinally extending slanted surface 69, while blade contacting members 70 include oppositely facing slanted surfaces 72. These slanted surfaces essentially define the initially slanted path 74 for blade 22. Slanted surfaces 72 of blade contacting members 70 are axially defined or limited by a ridge 73.

Merging from initially slanted path 74 is an essentially straight path 76 for blades 22 within chambers 46, as particularly illustrated in FIGS. 6, 7, and 10a through 10c. Straight path 76 is defined essentially between a longitudinally extending edge 75 of blade contacting member 70 and an oppositely facing rigid plane or frame member 84. Each chamber is defined by such oppositely facing rigid plane members 84, as particularly illustrated in the figures. Each such plane member 84, with the exception of the extreme end plane members, comprises a guide post 68 formed on one face thereof 92 and blade contacting member 70 formed on the opposite face thereof 90, as particularly illustrated in FIGS. 6 and 7. The extreme plane member 86 illustrated in FIG. 9 comprises only the blade contacting member 70, and extreme plane member 88 contains only guide post 68.

Figure 8:
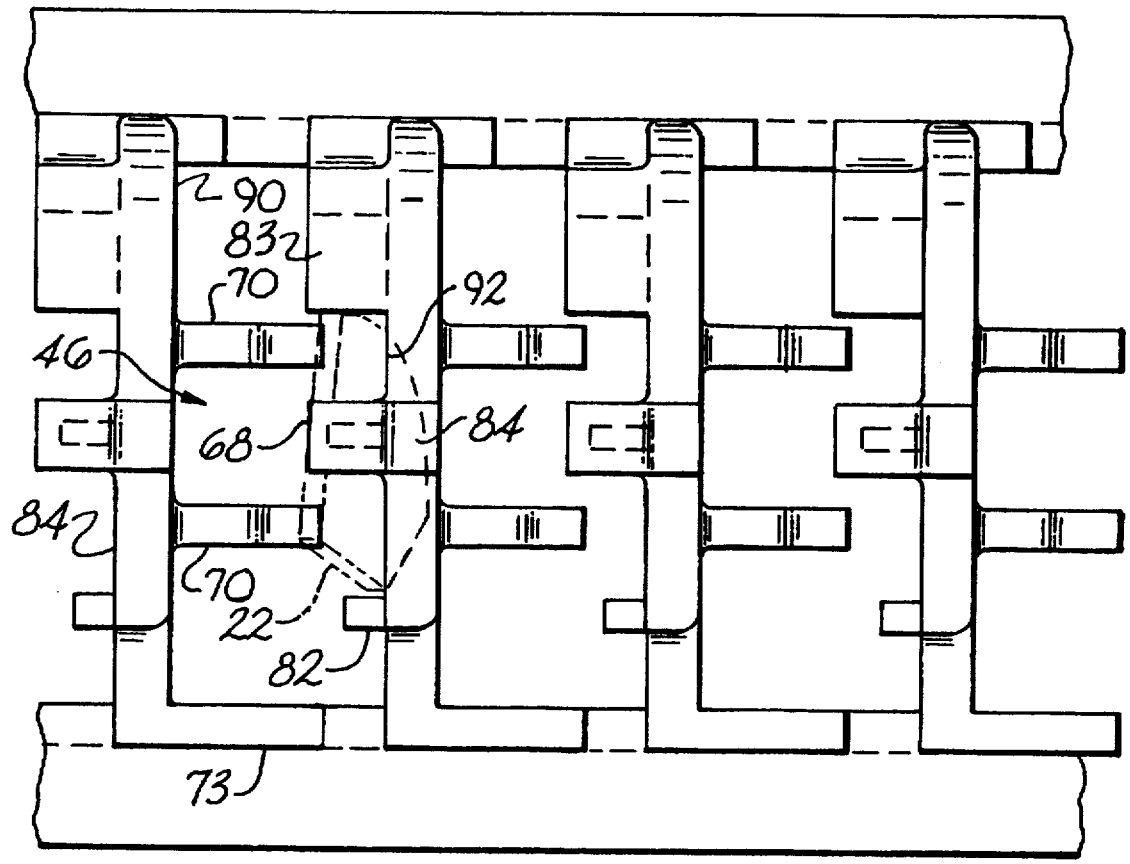
FIG. 8 is a top perspective view of the device illustrated in FIG. 5 taken along the lines indicated.

The configuration of the blade removal mechanism can be particularly seen in the top view of FIG. 8. This figure shows that guide post 68 is laterally offset from oppositely facing blade contacting members 70 such that blade 22 must be inserted at an angle along initially slanted path 74 to insert the blade within the individual slots 46. FIG. 8 also particularly illustrates rigid plane members 84 having blade contacting members 70 disposed on one face 90 thereof and guide post 68 disposed on the opposite face 92. As particularly illustrated in FIGS. 6, 7, and 10a through 10c, guide post 68 defines a recess 78 for blade 22 once the rear portion of the blade 22 disengages from the rear portion of boss member 26, as explained below.

Guide post 68 also comprises a retaining member or tab 80 which serves to hold blade 22 within chamber 46 upon removal of blade handle 24, and which also serves to prevent blades 22 from falling out of chamber 46 regardless of the orientation or position of the device. Retaining tab 80 includes a horizontally extending member 79 and a relatively small longitudinally extending nip 81. Recess 78 is defined essentially between nip 81 and the oppositely facing slanted surface 69 of guide post 68, as particularly seen in FIGS. 10a through 10c.

As particularly seen in FIGS. 6–7, 9, and 10a–10c, retaining tabs 80 extend above plane members 84 and include slanted surfaces 85 on their back faces. Slanted surfaces 83 aid in insertion of the scalpel handle and blade along initially slanted path 74.

As can be seen particularly in FIG. 5, each removal chamber 46 also includes guide walls 82 and 83 extending from plane members 84. Guide walls 82 and 83 serve to maintain blade 22 centered within chamber 46 such that guide post 68 engages boss member 26 and at least one of the slanted surfaces 72 of blade contacting members 70 engages blade 22 on either side of the boss member 26. Guide walls 82 and 83 also serve to limit movement or deflection of the knife handle 24 within chamber 46.

The operation of the device is depicted in the sequential illustrations of FIGS. 10a through 10c. Referring particularly to FIG. 10a, initially the surgical blade and knife 22, 24 are inserted into an individual chamber 46 such that guide post 68 contacts the boss member on the knife handle and the slanted surfaces 72 of the blade contacting members 70 engage the blade on either side of the boss member. In the first disengagement mode of blade removal mechanism 44, handle 24 and blade 22 must be inserted into the slot 46 at an angle so that blade 22 and the front portion of handle 24 move along the initially slanted path 74. For clarity sake, slanted paths 74, 76 are indicated diagrammatically by the pointed lines in FIG. 10c only. Upon further insertion of handle 24, blade 22 will contact the plane member 84 facing opposite of the blade contacting member 70 as it travels along the essentially straight path 76 defined in chamber 46. Thus, a bow or bend will be imparted to blade 22, as particularly seen in FIG. 10a. At this condition, slanted surfaces 72 of blade contacting members 70 tend to push or force blade 22 away from the blade handle boss member.

The second disengagement mode is illustrated particularly to FIG. 10b. Upon further insertion of handle 24 into the device, the rear edge of blade 22 will pass members 79 and 81 of retaining tab 80. Once the blade passes these members, it will disengage from the boss member and move into recess area 78, the blade then essentially assumes a more or less straight profile.

Referring particularly to FIG. 10c, once the rear end of blade 22 has been disengaged from boss member 26, the slotted portion 27 of the boss member can be disengaged from the narrow portion of the blade aperture 28 simply by withdrawing blade handle 24 from slot 46. Retaining member or tab 80 will hold blade 22 within slot 46 allowing relatively easy withdrawal of handle 24. Once handle 24 is completely disengaged from blade 22, the blade is free to fall into the blade receptacle area 42. However, as discussed, it is preferred that at least a portion of the blade 22 extend into chamber 46 so that the user can readily ascertain which chambers are free to accept used blades. In this regard, it may be preferred to define a blade abutment member 94 (FIG. 5) within the blade receptacle area 42 against which the knife edge of the blade may rest. Abutment member 94 also serves with guide walls 82 and 83 to maintain the removed blade centered within chamber 46 during operation of the device.

Figure 11:
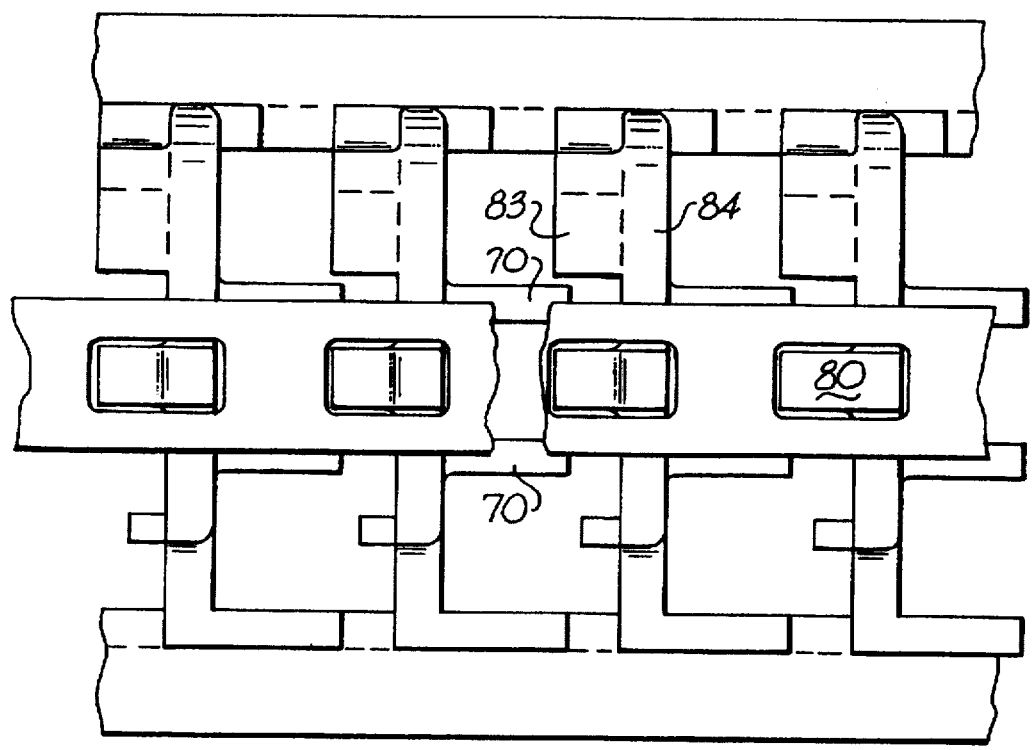
FIG. 11 is a top view of the blade removal device particularly illustrating the tape member disposed across the openings of the blade removal slots.
Figure 12:
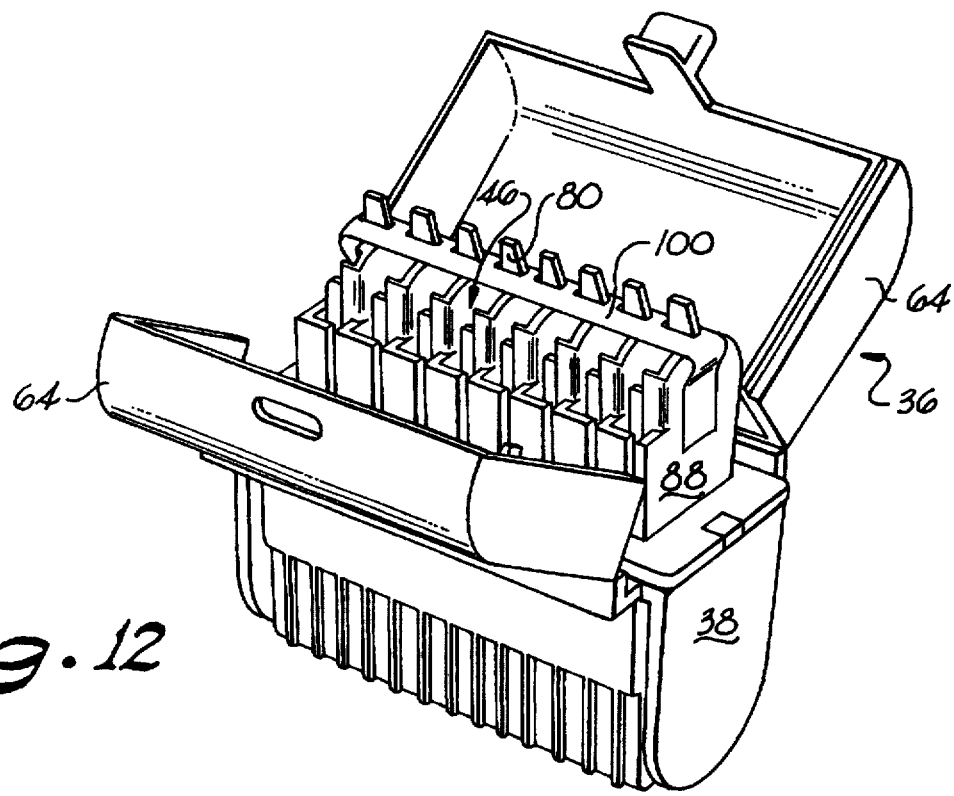
FIG. 12 is a full perspective view of the blade removal device shown in FIG. 11.

FIGS. 11 and 12 illustrate a preferred method for allowing the user of the device to quickly and accurately ascertain which of the chambers 46 are occupied by a scalpel blade 22. In this embodiment, a tape 100, or other suitable device, is placed across each of the openings into each slot 46. Tape 100 has holes or perforations therealong so that the tape can be fitted over tabs 80 of center post 68, as particularly illustrated in FIG. 12. Tape 100 can be attached through an adhesive or any other suitable means. In use, the user simply breaks the tape at whichever chamber 46 he intends to insert the scalpel blade and knife handle. Thus, the user can easily determine which chambers 46 are available merely by viewing the condition of the tape 100 at each of the chambers.

Once all of the chambers 46 contain used surgical blades, the user simply removes blade removal device 36 from its associated storage section 30 and replaces it with an empty device.

It may also be possible that the blade removal mechanism defining the individual chambers 46 is removably attached to the hand holding base portion 38 of device 36. In this manner, device 36 can be emptied of used blades by removing blade removal mechanism 44 from the hand holding base portion 38. For example, device 44 may be snap fitted or otherwise removably locked or engaged with base portion 38. Thus, blade removal device 36 can be recycled simply by emptying the used blades from the device.

It will be apparent to those skilled in the art that various modifications and variations can be made in the apparatus and method of the present invention without departing from the scope or spirit of the invention. For example, the device may include one or a plurality of individual blade removal slots and the handle section may comprise any manner of medical sharps containment and accountability devices. Thus, it is intended that the present invention cover the modifications and variations of the invention provided they come within the scope of the appended claims and their equivalents.

What is claimed is:

1. A medical sharps blade removal device, comprising:

a base portion having at least one blade removal chamber defined therein for receipt of a knife blade and handle;

a blade removal mechanism disposed within said at least one chamber, said blade removal mechanism comprising non-movable deflecting members defining a path for the knife blade through said blade removal mechanism and disposed to deflect the knife blade away from the knife handle in a first deflection mode and to remove the knife blade from the knife handle in a second deflection mode upon insertion and subsequent withdrawal of the knife handle from said at least one chamber without deflection of the knife handle by a user of said device; and members adapted to protect a user's hand operably disposed relative to said base portion and movable from a closed position to an open position.

2. A medical sharps blade removal device, comprising:

a base portion having at least one blade removal chamber defined therein for receipt of a knife blade and handle; and a blade removal mechanism disposed within said at least one chamber, said blade removal mechanism comprising non-movable deflecting members defining a path for the knife blade through said blade removal mechanism and disposed to deflect the knife blade away from the knife handle in a first deflection mode and to remove the knife blade from the knife handle in a second deflection mode upon insertion and subsequent withdrawal of the knife handle from said at least one chamber without deflection of the knife handle by a user of said device;

wherein said deflecting members comprise a rigid guide post centered between oppositely facing rigid blade contacting members; slanted surfaces defined on said blade contacting members which cooperate with said guide post to define an initial slanted path into said mechanism for the blade, said guide post disposed so as to contact a boss member of the knife handle and said slanted surfaces disposed so as to contact the blade on either side of the boss member upon the blade and handle being inserted into said initially slanted path in said first deflection mode; a substantially straight path merging from said slanted path whereby upon further insertion of the blade into said chamber the blade is forced along said straight path with said slanted surfaces thereby forcing said blade away from the boss member until the blade disengages from the boss member in said second deflection mode; and a recess defined in said guide post to allow the blade to fall away from the boss member upon disengaging therefrom.

3. The device as in claim 2, wherein said guide post further comprises a retaining member defined thereon to hold the blade within said mechanism upon removal of the handle from said mechanism.

4. The device as in claim 2, further comprising rigid guide walls disposed along said slanted and straight paths to maintain the blade and handle centered on said guide post and limit movement of the handle within said at least one chamber.

5. The device as in claim 2, further comprising oppositely facing rigid plane members, said guide post formed on one of said rigid plane members and said blade contacting members formed on said opposite rigid plane member, said slanted and straight paths defined between said rigid plane members.

6. A hand held medical sharps blade removal and storage device, comprising:

a base portion, said base portion defining a hand gripping section for a user to grasp and operate said device, said base portion further comprising a blade receptacle area defined therein;

hand protecting members operably disposed relative said base portion and movable from a closed position to an open position wherein said hand protecting members define a protected zone around said base portion for preventing injury to the user's hand when grasping said base portion;

a blade removal mechanism configured with said base portion and comprising a plurality of blade removal chambers disposed in communication with said blade receptacle area, each said chamber further comprising oppositely facing rigid members defining an initially slanted path and a substantially straight path merging from said slanted path for a blade inserted into each said chamber, said rigid members forcing the blade to disengage from its associated handle as the blade moves from said slanted path into said substantially straight path.

7. A hand held medical sharps blade removal and storage device, comprising:

a base portion, said base portion defining a hand gripping section for a user to grasp and operate said device, said base portion further comprising a blade receptacle area defined therein;

members adapted to protect a user's hand operably disposed relative said base portion and movable from a closed position to an open position wherein said members adapted to protect a user's hand define a protected zone around said base portion for preventing injury to the user's hand when grasping said base portion;

a blade removal mechanism configured with said base portion and comprising a plurality of blade removal chambers disposed in communication with said blade receptacle area, each said chamber further comprising oppositely facing rigid members defining an initially slanted path and a substantially straight path merging from said slanted path for a blade inserted into each said chamber, said rigid members forcing the blade to disengage from its associated handle as the blade moves from said slanted path into said substantially straight path, wherein said rigid members comprise a rigid guide post centered between oppositely facing rigid blade contacting members, said blade contacting members comprising slanted surfaces which cooperate with said guide post to define said initially slanted path, said guide post contacting a boss member of the handle and at least one of said slanted surfaces contacting the blade on either side of the boss member upon the blade and handle being inserted into said initially slanted path, each said chamber further comprising rigid planar members defining said substantially straight path whereby upon further insertion of the blade into said chamber the blade is forced along said straight path with said at least one slanted surfaces forcing said blade away from the boss member until the blade disengages from the boss member, said guide post further defining a recess to allow the blade to fall away from the boss member upon disengaging therefrom.

8. The device as in claim 7, wherein said guide posts further comprise a recess defined therein to allow the blade to fall away from the boss member upon disengaging therefrom, said guide posts further comprising a retaining lip defined therein to prevent the blade from falling out of said chamber.

9. The device as in claim 7, wherein each said chamber is defined between two said rigid planar members, each said planar member with the exception of the extreme end planar members comprises a said guide post formed on one face thereof and said blade contacting members formed on an opposite face thereof.

10. A hand held medical sharps blade removal and storage device, comprising:
 a base portion, said base portion defining a hand gripping section for a user to grasp and operate said device, said base portion further comprising a blade receptacle area defined therein;
 members adapted to protect a user's hand operably disposed relative said base portion and movable from a closed position to an open position wherein said members adapted to protect a user's hand define a protected zone around said base portion for preventing injury to the user's hand when grasping said base portion;
 a blade removal mechanism configured with said base portion and comprising a plurality of blade removal chambers disposed in communication with said blade receptacle area, each said chamber further comprising oppositely facing rigid members defining an initially slanted path and a substantially straight path merging from said slanted path for a blade inserted into each said chamber, said rigid members forcing the blade to disengage from its associated handle as the blade moves from said slanted path into said substantially straight path, and
 a removable medical sharps storage section attached to said base portion.

11. The device as in claim 10, wherein said storage section comprises hinged halves and a locking mechanism for locking said halves in a closed position, and a medical sharps storage area defined between said halves.

12. The device as in claim 11, wherein at least one of said halves comprises a sharps accountability device.

13. A medical sharps removal and storage system, comprising:
 a storage compartment defining a storage area for medical sharps;
 a blade removal insert device removably mated with said storage compartment, said blade removal insert device comprising a base portion, a blade removal mechanism attached to said base portion, a blade receptacle area defined in said base portion, and selectively positionable oppositely facing hand protecting members, said blade removal mechanism accessible to a user of said system through positioning said hand protecting members to an open position; and
 said blade removal mechanism further comprising a disengaging mechanism configured for allowing an operator to remove a blade from a surgical knife handle by inserting the blade and attached handle into said blade removal insert device and withdrawing the handle from said blade removal insert device with the blade being retained in said blade receptacle area.

14. The system as in claim 13, wherein said blade removal mechanism comprises a plurality of blade removal chambers disposed in communication with said blade receptacle area, each said chamber further comprising oppositely facing rigid members defining an initially slanted path and a substantially straight path merging from said slanted path for a blade inserted into said chamber, said rigid members forcing the blade to disengage from its associated handle upon insertion of the blade into said chamber.

15. The system as in claim 14, further comprising a piercable tape member disposed across said chambers so that a user can tell which of said chambers are used by viewing the condition of said tape member at said respective said chambers.

16. The system as in claim 13, wherein said rigid members comprise a rigid guide post centered between oppositely facing rigid blade contacting members, said blade contacting members comprising slanted surfaces which cooperate with said guide post to define said initially slanted path, said guide post contacting a boss member of the handle and at least one of said slanted surfaces contacting the blade on either side of the boss member upon the blade and handle being inserted into said initially slanted path, each said chamber further comprising rigid planar members defining said substantially straight path whereby upon further insertion of the blade into said chamber the blade is forced along said straight path with said at least one slanted surfaces forcing said blade away from the boss member until the blade disengages from the boss member, said guide post further defining a recess to allow the blade to fall away from the boss member upon disengaging therefrom.

17. The system as in claim 16, wherein said guide posts further comprise a recess defined therein to allow the blade to fall away from the boss member upon disengaging therefrom, said guide posts further comprising a retaining lip defined therein to prevent the blade from falling out of said chamber.

18. The system as in claim 13, wherein said storage compartment comprises a handle section, said handle section comprising hinged halves and a locking mechanism for locking said halves in a closed position, said storage area defined between said halves.

19. The system as in claim 18, wherein said handle section comprises a receiving well for said blade removal insert device, and a hand holding base portion slidably engaging within said receiving well, said hand protecting members comprising hinged locking cover components which open to a position substantially transverse to a longitudinal plane through said hand holding base portion, said blade removal mechanism accessible by opening said cover components.

20. The system as in claim 13, wherein at least components of said blade removal insert device are formed of a substantially transparent material.

* * * * *